United States Patent [19]

Campbell et al.

[11] Patent Number: 4,478,817

[45] Date of Patent: Oct. 23, 1984

[54] DETECTING OR QUANTIFYING SUBSTANCES USING LABELLING TECHNIQUES

[75] Inventors: Anthony K. Campbell; John S. A. Simpson, both of Cardiff; James S. Woodhead, Machen, all of Wales

[73] Assignee: The Welsh National School of Medicine, Cardiff, Wales

[21] Appl. No.: 961,389

[22] Filed: Nov. 14, 1978

[30] Foreign Application Priority Data

Nov. 17, 1977 [GB] United Kingdom ............... 47839/77

[51] Int. Cl.³ ..................... G01N 31/00; G01N 31/22; G01N 33/48; G01N 33/54; G01N 33/56
[52] U.S. Cl. ..................................... 424/7.1; 436/547; 436/800; 435/7
[58] Field of Search ................... 23/230 B; 424/1, 1.5, 424/7, 8, 12, 7.1; 250/302, 361 C, 373, 458; 435/7, 8; 436/547

[56] References Cited

U.S. PATENT DOCUMENTS

| | | | |
|---|---|---|---|
| 3,992,631 | 11/1976 | Hartz | 424/12 X |
| 4,000,252 | 12/1976 | Kosak | 424/12 X |
| 4,025,310 | 5/1977 | Bolz | 424/12 X |
| 4,036,946 | 7/1977 | Kleinerman | 424/12 X |
| 4,041,146 | 8/1977 | Giaever | 23/230 B X |
| 4,104,029 | 8/1978 | Maier | 424/12 X |
| 4,128,628 | 12/1978 | Brooker | 23/230 B X |
| 4,153,675 | 5/1979 | Kleinerman | 424/8 |
| 4,160,645 | 7/1979 | Ullman | 23/230 B |
| 4,172,827 | 10/1979 | Giaever | 260/112 B X |
| 4,208,479 | 6/1980 | Zuk | 23/230 B X |

OTHER PUBLICATIONS

Chappelle, Biochem. Med., vol. 2, 1968 pp. 41-52.

*Primary Examiner*—Albert T. Meyers
*Assistant Examiner*—Kathleen S. McCowin
*Attorney, Agent, or Firm*—Young & Thompson

[57] ABSTRACT

The invention relates to a method of detecting, analyzing, quantifying or locating a protein, antibody, antigen, hapten, hormone, metabolite, nucleic acid or steroid, in which the substance of interest is linked to a chemiluminescent or bio-luminescent label. A luminescent reaction is then triggered by the addition of an oxidizing agent or a catalyst and the emitted light is observed in order to provide information about the substance. The invention employs a luminescent reagent which consists of antibodies labelled with a luminescent material such as luminol. The luminescent reagent can be used to quantify antigens in an immunological assay. The luminescent labelled antibodies selectively bind to the antigens and the amount of light emitted in a luminescent reaction gives an indication of the amount of antigens present. A luminescent labelled substance can also be reacted with an antibody or antigen labelled with a fluorescent material in order to carry out a homogeneous assay.

20 Claims, No Drawings

DETECTING OR QUANTIFYING SUBSTANCES USING LABELLING TECHNIQUES

This invention relates to methods and equipment designed for use in the analysis, assay, or location of proteins and other substances of biological interest by linking ("labelling") them to another molecule or molecules which can take part in a reaction resulting in the emission of light. The labelled substance, to be termed "luminescent reagent", may be used in various types of biological investigations; such as:

(a) Immunoassay and protein binding assays.
(b) Turnover of substances in vivo and in vitro.
(c) Localisation of substances histologically.
(d) Tracing of substances undergoing redistribution in biological systems, or in vitro separation procedures such as centrifugation, chromatography and electrophoresis.

In the context of this Specification the term "luminescent reagent" is used to described a complex between a molecule not normally capable of taking part in a luminescent reaction and another molecule which is capable of participating in a luminescent reaction. For the purposes of this invention, and this specification and the appended claims, a luminescent reaction is defined as one which involves a chemical reaction that results in the emission of light. The amount of the "luminescent reagent" is measured by recording the light emitted after producing the appropriate conditions required for the luminescent reaction to take place. The light may be intense or quite weak, but of sufficient duration, to enable the light to be detected and measured. This luminescent is to be distinguished clearly from fluorescence and phosphorescence.

A luminescent reaction is normally one between at least two molecules (S and L) with or without other reagents, cofactors, or a catalyst (D) or under the influence of a physical trigger. L is the substance which generates light, such as luminol. S is the substance which reacts with L to cause excitation, for example oxygen or hydrogen peroxide. D (if present) is a cofactor, and/or catalyst or trigger such as an enzyme, a luciferase, or potassium ferricyanide. The reaction between L and S results in the conversion of L to an excited molecule L* and the return of this excited molecule to a non-excited state results in the emission of a photon. The reaction between L and S and the decay of L* to the non-excited state may take place spontaneously or may require the presence of the cofactor or catalyst D, or a physical trigger such as temperature or radiation. An example of such a reaction is the oxidation by $H_2O_2$ of luminol. The catalysts and cofactors are often inorganic compounds as here, but may also be extracted from biological material such as the enzyme peroxidase which catalyses the luminescent reaction involving luminol.

The formation and measurement of the "luminescent reagent" can be described by the following general reactions:

The synthesis of the "luminescent reagent" may be written thus:

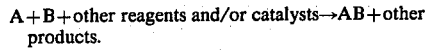

Where

A = substance not normally capable of participating in a luminescent reaction,
B = substance capable of taking part in a luminescent reaction, and
AB = "Luminescent reagent".

A is normally (but not always) the substance of interest, requiring analysis or detection, and may be of biological or chemical nature. For example, it may be a protein, antibody, antigen, hapten, hormone, a drug or other substance of pharmacological interest, a metabolite, nucleic acid, or in general any macromolecule or non-polymeric molecule.

B is normally (but not always) the label, and is essentially stable in terms of luminescence, and any other possible reactions which might affect the procedures. B may consist of L and/or S and/or D, and in general may comprise any one or more stable components of a multiple-component luminescent reagent. Usually the synthetic reaction for AB will omit one or more of the essential components or ingredients, such that the luminescent reaction can be triggered by adding the missing component(s).

In some cases the substance A alone requires to be analysed, measured or detected. The stable label B will then normally be added to A at an earlier stage in the procedure, and the remaining component(s) of the luminescent reagent will be added at the moment when the emitted light is to be sensed.

In other cases the substance A is to be reacted with another substance C, and either A or C may be of interest, and require analysis or detection. The reaction to be analysed may be written:

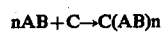

Where
C is a substance, not normally luminescent, which reacts with A.
n = number of molecules of AB which combine with C.

The analysis involves the measurement of C(AB)n or the loss of nAB from the initial pool of AB molecules.

In the final determination of the "luminescent reagent" the reaction may be written:

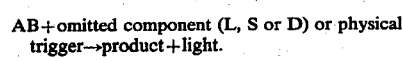

The amount of light emitted (luminescence) can be related directly to the concentration of AB added to the reaction mixture.

Currently the most popular substance for labelling proteins is a radioactive isotope such as $^{125}I$. With this method the amount of AB reaction with C, as shown above, is determined by measurement of radioactivity. Radioactive reagents have three major disadvantages. Firstly, the method of labelling involves the use of highly radioactive and hence potentially hazardous reagents. Secondly, the shelf life of the radioactively labelled substance is often relatively short not only because by its very nature the radioactive isotope is continuously decaying but also radioactively labelled proteins are often unstable. Thirdly, it is often difficult to label proteins sufficiently to provide a sensitively and rapidly detectable reagent. The measurement of luminescence is both highly sensitive and very rapid, the time of measurement being of the order of seconds rather than the several minutes normally required for measurement of radioactivity. The attachment, either covalently or non-covalently, to substances not normally capable of taking part in a luminescent reaction of a substance which is capable of taking part in a luminescent reaction provides a reagent which can be rapidly measured in very small quantities.

A substance to be used as a "label" in the preparation of a "luminescent reagent" should preferably satisfy four requirements:

(a) It should be capable of taking part in a luminescent reaction.

(b) It should be possible to attach it to the substance not normally luminescent to form a reagent which is relatively stable.

(c) It should still be able to participate in a luminescent reaction after being coupled to form the reagent.

(d) It should not significantly alter the properties of the molecule to which it is attached.

Broadly stated the invention consists of a method of detecting, analysing, quantifying or locating a substance, in which the substance, or an associated substance, is labelled by linking one or more components which can participate in a luminescent reaction, and a luminescent reaction is subsequently triggered, the emitted light being sensed, observed, measured and/or recorded, to provide information concerning the substance of interest. Preferably, the labelling of the substance produces a luminescent reagent.

The reaction may be triggered chemically by means of a chemical reagent or catalyst, or by a change in pH, or it may be triggered physically, for example by heat or radiation. In some preferred embodiments the luminescent reagent comprises at least two chemical components, with or without a cofactor or catalyst, and the label comprises an incomplete number of the components or elements, the luminescent reaction being triggered by subsequent addition of the essential missing component(s) or element(s).

In any case the labelling component(s) of the reaction are preferably stable, and do not significantly alter or effect the substance to which they are linked.

Preferably, the substance of interest or the associated substance is a protein, antibody, antigen, hapten, hormone, metabolite, nucleic acid or steroid. In a particularly preferred aspect of the invention, the luminescent reagent comprises antibodies labelled with a luminescent material. The labelled antibodies are preferably used to detect, analyse, quantify or locate corresponding antigens.

In a further aspect of the invention, there is provided a luminescent reagent comprising antibodies labelled with a luminescent label. Preferably, at least 60%, more preferably at least 80% of the antibodies in the luminescent reagent are biologically active, i.e. they are capable of binding to corresponding antigens.

The labelled antibodies may be prepared from a medium containing the antibodies, such as serum, by contacting the medium with the corresponding antigens, preferably in a solid phase, to cause antibody-antigen association, a luminescent label being added before or after association occurs, and subsequently dissociating the labelled antibodies from the antigens. The antigens only bind the antibodies specific to them, and the subsequent dissociation produces luminescent labelled antibodies with a high degree of biological activity. The dissociation may take place by adjusting the pH of the system or by a reduction reaction. This preparation effectively produces "purified" labelled antibodies due to the selectivity of the antigen-antibody reaction. The antigens are preferably linked to a solid phase immunoadsorbent, and the luminescent label may either be added to the antibody-containing medium before or after the medium contacts the antigens. The result is the same in that the remaining components of the medium which do not bind with the antigens may be washed away, leaving a labelled antigen-antibody complex from which labelled antibodies can be dissociated. This type of purification is known as immunological purification and, where the antigen is itself an immunoglobulin, it can be used to produce labelled anti-immunoglobulins which can be used as universal reagents in immunological assays.

A labelled antibody is by nature an immunoglobulin. In most instances these can be directed at antigens such as protein hormones, haptens or other molecules. In special cases immunoglobulins may themselves be used as antigens, e.g. rabbit IgG (an immunoglobulin) will behave as an antigen when injected into sheep. The antibody produced will bind rabbit IgG which will include specific antibodies raised in rabbits. This for example alphafoetoprotein (AFP) may be quantified by the binding of labelled rabbit antibody to AFP. Alternatively, AFP can be quantified by first reacting with rabbit anti-AFP antibody (unlabelled) and then detecting the complex by the uptake of labelled sheep (anti rabbit IgG) antibody. This indirect procedure has the advantage that many immunological assay systems utilize rabbit antibodies. Instead of labelling these individually, the labelled sheep-(anti rabbit IgG) antibody can be used as a "universal" reagent. Other preferred universal reagents are antibodies to guinea pig IgG, sheep IgG, goat IgG and donkey IgG, since antisera to certain molecules may be raised in any of these species. Most commonly used universal reagents would however be sheep-(anti rabbit IgG) and sheep anti-(guinea pig IgG). The "purified" labelled antibody preparation is extremely stable, especially if stored at a pH of from about 7 to 8 and at a temperature below 0° C., preferably about −20° C., and has a shelf life of many months. This is a great advantage over radio-isotopes which have a limited shelf life due to their continual decay. A further advantage is that radio-isotopes can damage proteins, whereas the luminescent labels do not. Labelled antibodies may be obtained for the following hormones and proteins: Insulin, Growth hormone, Parathyroid hormone, Follicle stimulating hormone, Luteinizing hormone, Thyroid stimulating hormone, Adrenocorticotrophic hormone, Glucagon, Prolactin, Galcitonin, Ferritin, Alphafetoprotein, Human immunoglobulin G (IgG), Rabbit IgG, Sheep IgG, Guinea pig IgG, Donkey IgG, Human Immunoglobulins E and M, Cell surface antigens. Labelled antibodies to haptens can also be produced which bind to drugs or cyclic nucleotides. The labelled antibodies derived from these hormones, proteins and haptens are particularly useful for carrying out rapid immunological assays. Such assays are conveniently carried out by using so-called immunoradiometric or "two-site assay".

According to a further aspect of the invention, therefore, there is provided a method of carrying out an assay in which a medium containing the substance of interest, such as antigens, is contacted with antibodies so that the antibodies selectively bind the substance, the product of the binding reaction is subsequently contacted with luminescent labelled antibodies and a luminescent reaction is triggered, the amount of the substance of interest which is present being indicated by the amount of luminescence.

Preferably the substance of interest is bound to antibodies on a solid phase which may be cellulose powder or the wall of a reaction vessel, such as a glass or plastics tube. Other substances in the medium are not bound by the antibodies and so can be washed away.

This "two-site assay" technique is especially effective using luminol or a derivative thereof as the luminescent label, coupled to sheep (anti-rabbit IgG) antibody. The performance of this luminol-labelled antibody is unaffected following 9 months storage at −20° C.

The variety of luminescent labels which may be used in the present invention is extremely wide.

In the present invention luminescent labels can be conveniently divided into two classes:
1. Chemi-Luminescent labels
2. Bio-Luminescent labels.

Chemi-Luminescent labels include inorganic or organic molecules which can react with other molecules to produce light. These substances may be extracted from biological sources but in this case are not normally involved in the emission of light in their natural environment. The luminescent reaction involving the chemi-luminescent label is triggered by addition of the appropriate reagent or reagents.

The trigger may be an oxidising agent preferably in an alkaline medium, or a catalyst. A preferred chemiluminescent label is a compound of the general formula (I)(a) or (I)(b).

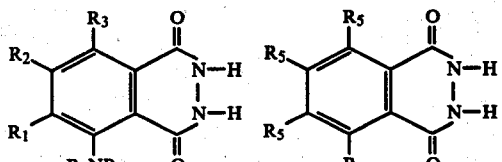

(I)(a)    (I)(b)

in which each of $R_1$, $R_2$ and $R_3$ is H, $C_1$–$C_{10}$ optionally substituted alkyl or alkenyl, amino, substituted amino, carboxyl or hydroxyl, each of $R_4$ and $R_5$ is the same as $R_1$, $R_2$ or $R_3$, or is a diazo-linkage, a hemi-dicarboxylate linkage, an amide linkage, an organic acid halide, or an isothiocyanate group, with the proviso that at least one of $R_1$ to $R_5$ is amino or substituted amino. Preferably, the compound is luminol ($R_1$ to $R_3$ are each hydrogen).

Preferably, each of $R_4$ and $R_5$ is amino substituted by hemisuccinate, amino ethyl-, or chloroacetyl.

An important advantage of the compounds of formula (I) is that they can readily form bridges with antibodies by, for example, peptide linkages. Peptide bond formation may be carried out by using mixed anhydride, carbodiimide, suberimidate or hemisuccinate coupling. Other preferred chemiluminescent labels are (i) lophine and derivatives thereof, i.e. compounds of the general formula (II)

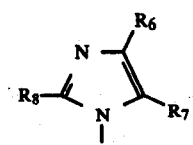

in which each of $R_6$, $R_7$ and $R_8$ is an optionally substituted phenyl radical (ii) lucigenin and derivatives thereof, i.e. compounds of the general formula (III)

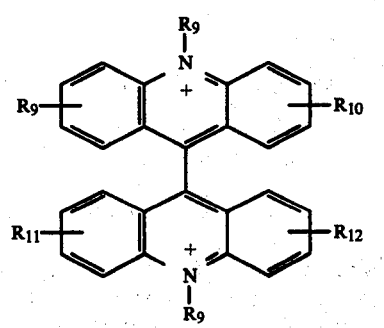

in which each of $R_9$, $R_{10}$, $R_{11}$ and $R_{12}$ is the same as $R_1$, $R_2$, $R_3$, $R_4$ or $R_5$ as defined in formula (I)

(iii) acridinium compounds of the general formula (IV)

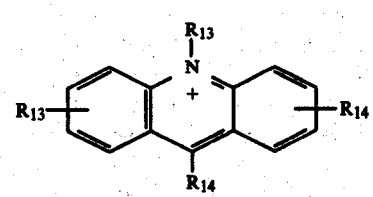

in which each of $R_{13}$ and $R_{14}$ is the same as $R_1$, $R_2$, $R_3$, $R_4$ and $R_5$, as defined in formula (I)

(iv) trans-azodicarboxylates of the general formula (V)

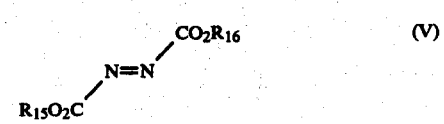

in which each of $R_{15}$ and $R_{16}$ is H or lower alkyl (v) oxalate esters of the general formula (VI)

in which each of $R_{17}$ and $R_{18}$ is lower alkyl.

(vi) pyrogallol

Preferred triggers are hydrogen peroxide, potassium permanganate, potassium ferricyanide, or oxygen in the presence of dimethyl sulphoxide. Catalysts from biological sources, such as enzymes, may be used as triggers. A preferred catalyst is peroxidase.

Examples of reactions involving luminol which result is the emission of light are:

1

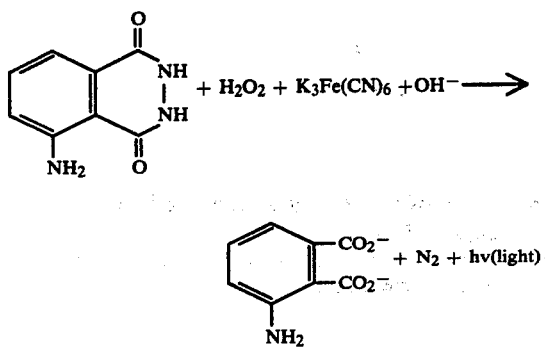

2 luminol + H$_2$O$_2$ + KMnO$_4$ ⟶ oxidised luminol + hv(light)

3 luminol + H$_2$O$_2$ + peroxidase ⟶ oxidised luminol + hv(light)

The luminescent reaction may also be triggered by a change in pH or in the physical conditions such as temperature, polarity of the solvent and emissions such as X-rays, γ rays and particles from radioactive isotopes.

Bio-luminescent labels are components which take part in a bio-luminescent reaction, which is defined as a reaction resulting in the production of light in which at least one of the components has been extracted from a biological source and which in its natural environment is involved in the production of light. Under this heading are included reactions involving synthetic compound of identical or similar structures which have been synthesised in order to mimic the naturally occurring compound.

Preferred bio-luminescent labels are
 (i) firefly luciferin, and derivatives thereof, of the general formula (VII)

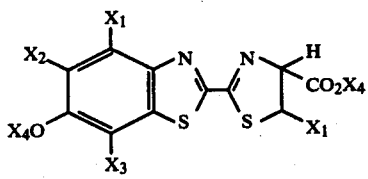 (VII)

in which each of X$_1$, X$_2$, X$_3$ and X$_4$ has the same meaning as R$_1$, R$_2$, R$_3$, R$_4$ and R$_5$ in formula (I), and, (ii) Coelenterate chromophores of the general formula (VIII)

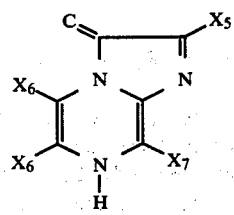 (VIII)

in which each of X$_5$, X$_6$ and X$_7$ has the same meaning as R$_1$, R$_2$, R$_3$, R$_4$, and R$_5$, in formula (I), or is

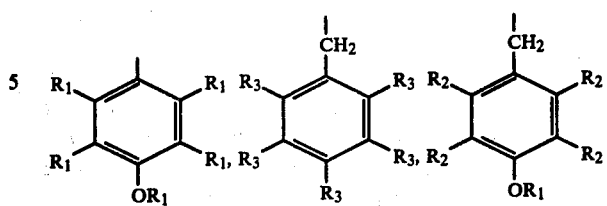

In general, any stable luciferin or coelenterate derivatives will be suitable.

A large number of bio-luminescent reactions require oxygen as part of the reaction and an example is as follows:

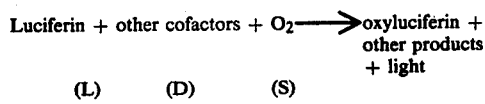

The reaction is catalysed by an enzyme known as a luciferase. Other oxidising agents such as those used for the chemi-luminescent labels, may be used in the reaction.

The luminescent reactions isolated from some luminous organisms however do not conform to this scheme. In some instances of the present invention these reactions are triggered by addition of the appropriate cofactors. An example is the addition of calcium ions to the photo-proteins isolated from a number of coelenterates:

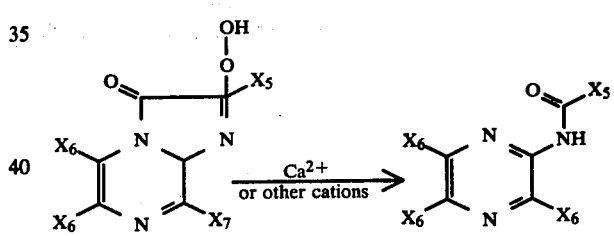

in which each of X$_5$, X$_6$ and X$_7$ is as defined in formula (VII).

In this invention any one of the components involved in a luminescent reaction may be used as a label to form a "luminescent reagent". Thus a chemi-luminescent label may be an organic compound such as luminol, an inorganic ion or molecule, or a catalyst such as the enzyme peroxidase. Similarly a bio-luminescent label may be any luciferin or luciferase, it may be a structural analogue of a luciferin, or it may be one of the following co-factors:

| 1. Firefly  | ATP |
|---|---|
| 2. Bacteria | NADH |
|             | FMNH |
|             | R.CHO where R = aliphatic group |
| 3. Fungi    | NADH |
|             | NADPH |

In performing the invention the amount of luminescent reagent (AB) is normally determined by placing a sample in a tube, omitting one or more components, or the trigger needed for the luminescent reaction. The reaction is then triggered, physically, or chemically by the addition of the remaining component(s) or catalyst. The light emitted may be located or quantified by a standard measuring device such as a photo multiplier tube the signal from which is fed to and displayed or recorded on a recorder, oscilloscope, or scalar. The light may also in some cases be observed by the naked eye, or recorded on a photographic plate, or by means of an image intensifier especially when positional information is required, for example the position of maximum light intensity for histological purposes, or the colour, or the intensity relative to a standard.

The present invention involves the application of "luminescent reagents" to a variety of procedures, including in particular the following four major analytical problems.

1. Immunoassay and protein binding assays.

This analytical procedure is in common use and normally involves the reaction of the molecule requiring analysis (A) with the binding protein (C), which in the case of immunoassay is an antibody.

The essential feature of this method of analysis is that it is necessary to separate the A-bound-to-antibody from the free A or to separate bound antibody from free antibody. The reaction is quantified by labelling either the antibody, A, or another molecule which can react with the free or bound moieties after separation. The label will be either a chemi- or bio-luminescent label as defined above. An example of this type of assay is the "two-site assay" described above.

2. Turnover.

There are many situations where it is necessary to quantitatively follow the turnover of a molecule in vivo or in vitro. The molecule may be of biological origin or it may be a pharmacological compound. In order to measure the turnover of such substances a small, standard quantity of the substance labelled with a chemi- or bio-luminescent label (as defined above) is added to medium containing the unlabelled substance. The turnover of the substance can then be measured by measuring the loss of the labelled substance.

3. Localisation of substances histologically.

In order to localise a substance inside or outside a cell using a "luminescent reagent" the appropriate reagent (e.g. a labelled antibody) is added to a tissue preparation and after washing is examined under a microscope. The "Luminescent reagent" is then located by eye or by using an image intensifier; the image can then be photographed.

4. Tracing of substances undergoing redistribution.

In a number of biological systems and in vitro separation procedures, such as centrifugation, chromatography, and electrophoresis it is necessary to follow a substance undergoing redistribution. This is done by adding to the initial preparation a small standard quantity of the substance labelled with a chemi- or bio-luminescent label. The distribution of the substance being studied can then be monitored by following the distribution of the "luminescent reagent".

The invention also has considerable value in carrying out homogeneous assays, particularly for small molecules. Such assays have the advantages of rapid analysis and no requirement for a separation stage.

In a conventional radioimmunoassay technique an antigen is reacted with a limited quantity of binding reagent (i.e. antibody). The proportion of antigen bound varies inversely with the concentration added. The reaction is monitored by the incorporation of a trace amount of labelled antigen. An essential feature of the technique is the ability to separate bound antigen from unbound antigen.

A homogeneous assay is designed so that a property of the labelled antigen is altered upon reaction with antibody. Thus the reaction is monitored without the necessity of separation of bound and unbound fractions. Radioisotope labels can not be used in this way. In a homogeneous assay the light emitted from a luminescent labelled antigen (or antibody) causes the emission of light of different wavelength from antibody (or antigen) labelled with a fluorescent molecule. Thus the use of an appropriate filter in the detection apparatus would result in the measurement of light derived from the fluorescence resulting from antigen-antibody interaction. The system is homogeneous because it is unnecessary to remove unreacted antigen from the assay since its emission is of shorter wavelength and not therefore registered.

Thus, the invention also provides a method of carrying out a homogeneous assay in which a luminescent labelled substance is reacted with an antibody or antigen labelled with a fluorescent label and a luminescent reaction is triggered, the energy from the luminescent reaction exciting the fluorescent label on the antibody or antigen to produce a wavelength shift in light emission or a change in quantum yield.

Preferably the antibody or antigen is labelled with fluoroscein. The luminescent reaction is conveniently triggered by adding peroxidase.

Preferably, the substance of interest is a hapten, and includes the following substances: Cyclic nucleotides (cyclic AMP, cyclic GMP and cyclic CMP), 25-hydroxycholecalciferol, 1,25-dihydroxycholecalciferol Throxine, Triiodothyronine, Progesterone, Oestradiol, Oestriol, Testosterone, Aldosterone, Cortisol, Glycocholic acid, Taurocholic acid, Barbiturates, Salicylates, Phenitoin, Morphine, Heroin, Methotrexate, Digoxin.

The preferred chemiluminescent label for the haptens, especially thyroxine, is an oxalate ester.

EXAMPLES

1. Excitation of a luminol-Sheep (anti-rabbit IgG)

A luminescent reagent is prepared by coupling the diazonium salt of luminol to sheep (anti-rabbit IgG) antibody. The luminescent reaction is triggered by exciting the reagent with oxygen in the presence of alkali, light being emitted at a wavelength of 400–500 nm. and detected with a photon counting meter.

The light emission from the reagent following excitation is extremely rapid, less than 2 seconds being required to quantify accurately the luminol present.

More detailed examples of the invention are as follows:

2. Immunoassay-Assay of parathyroid hormone using luminol labelled antibodies.

a. General method

A method for measuring the concentration of parathyroid hormone in human serum is known (Woodhead et al; Brit. Med. Bull. 30, 44–49, 1974), using antibodies labelled with $^{125}I$.

b. Preparation of antibodies labelled with luminol.

The principle chemical reaction described here is a diazotisation between luminol and antibodies to human parathyroid hormone. 2 mg of luminol are suspended in 1 ml of NHCl at 0° C. 10 mg of $NaNO_2$ are added and the solution gently mixed for approximately 3 min. The pH is then adjusted to 8.0–9.0 with NaOH. 2 mls of a solution of antibodies to human parathyroid hormone bound to human parathyroid hormone on aminocellulose (immunoadsorbant) in 0.2M sodium borate, pH 8.2 are then added. After incubating this mixture for approximately 16 h at 4° C. the immunoadsorbant is washed four times with borate buffer. The immunoadsorbent is then washed three times with 0.9% (w/v) sodium chloride. The antibodies labelled with luminol are eluted with buffer at pH 2.

c. Assay of parathyroid hormone (PTH)

This is done by a method similar to a immunoradiometric assay except that the antibodies are labelled with luminol rather than $^{125}$I. PTH standards (0.08–50 ng/ml) are made up in NIGP (20.6 g sodium barbitone, 10 g NaCl, 1 g sodium azide, 2 g human serum albumin, 40 mg non-immune guinea pig y-globulin, made up to 2 l, pH adjusted to 8.0 with 1.0N HCl). 100 μl of each standard is put into Beckman polyethylene tube (EET 23) in quadruplicate. 50 μl of sample to be assayed is put into similar tubes and 50 μl NIGP buffer added. 10 μl of "luminescent reagent" (PTH antibody labelled with luminol) are added. After mixing, the tubes are incubated for 3 days at 4° C. 50 μl of PTH ImAd (PTH covalently linked to cellulose) are added. After 20 min the tubes are centrifuged for 1 min and 90 μl for the supernatant assayed for "luminescent reagent" by assaying for luminol.

d. Assay of "luminescent reagent"

90 μl of the supernatant described above is added to 900 μl of N/10 NaOH, 10 μl of $H_2O_2$ are added and the tube placed in front of a photomultiplier tube. The total counts recorded in the first 10s after the addition of 1 ml of 1 mM $K_3$ Fe(CN)$_6$ are plotted against PTH concentration. The values in the samples can then be read off this standard curve.

3. Turnover-Turnover of albumin in a liver homogenate

Bovine serum albumin (BSA) labelled with luminol is prepared as described in Examples 2 for antibodies to PTH. An homogenate of rat liver (2:1 w/v) is prepared in 150 mM KCl, 2 mM MgCl$_2$, 1 mM mercaptoethanol, 20 mM tris pH 7.4 1 ml samples are placed in Luckam LP3 plastic tubes, 10 μl samples of BSA labelled with luminol+10 μl of unlabelled BSA (0.01–100 mg/ml) are added and the tubes incubated at 37° C. for up to 60 min. After a defined interval the albumin is precipitated by addition of an equal volume of saturated (NH$_4$)$_2$SO$_4$. The tubes are then centrifuged, the pellet washed and redissolved in 0.5 ml N/50 naOH. 100 μl samples are taken for assay of the "luminescent reagent" as described in Example 2 for luminol labelled antibodies. The decrease in luminescent activity from this pellet is a measure of the rate of destruction of the albumin.

4. Histochemical localisation-Localisation of antigens on erythrocytes

Antibodies to human erythrocytes are labelled with luminol as described in Example 2 for antibodies to PTH. 10 μl of this "luminescent reagent" are added to 1 ml 0.9% (w/v) NaCl containing $10^8$ human erythrocytes. After a 30 min incubation at 37° C. the cells are centrifuged and washed three times with 0.9% (w/v) NaCl. The cells are then smeared on to a microscope slide and observed under a light microscope with an image intensifier attachment. 1 mM KMnO$_4$ is added to stimulate the luminescence of the luminol. Cells with antibodies attached to them (and hence antigens on their cell surface) emit light which is visualised by the image intensifier and then photographed. The cells containing antigens can then be localised by comparing the image intensified photograph with a photograph taken under phase contrast.

5. Distribution of cell membrane antigens during fractionation of rat adipocytes.

Antibodies to rat adipocytes are labelled with luminol as described in Example 2 for antibodies to PTH. 10 μl samples of the "luminescent reagent" are added to 1 ml of a solution containing 144 mM Na$^+$, 5.9 mM K$^+$, 1.2 mM Mg$^{2+}$, 2.6 mM Ca$^{2+}$, 128.9 mM Cl$^-$, 1.2 mM SO$_4^{2-}$, 1.2 mM pi, 25 mM HCO$_3^-$, 4% BSA 2/v, pH 7.4 and $10^6$–$10^7$ rat adipocytes. After a 30 min incubation at 37° C. the suspension is centrifuged and the cells washed three times. The cells are then homogenised in 5 ml 150 mM KCl, 2 mM MgCl$_2$, 1 mM mercaptoethanol, 20 mM tris, pH 7.4. A convential differential centrifugation procedure is carried out, the 500 g, 10,000 g, 100,00 g pellets and 100,000 g supernatant being collected. 100 μl samples of each fraction are then assayed for luminol as described in Example 2. A comparison of the quantity of luminol in each fraction compared with that on the whole cells enables a quantitative estimate of the amount of cell membrane antigens in each fraction to be obtained.

6. 2-Site Assay of Alphafoetoprotein Using Luminol Labelled Antibodies

An immunoglobulin fraction of an antiserum to alphafoetoprotein (AFP) is prepared by sodium sulphate precipitation. The precipitate containing antibodies to AFP is coupled covalently using glutaraldehyde to a silane derivative of borosilicate glase in the form of reaction tubes. Samples containing AFP are incubated for a period of 3 hours in the tubes during which time the AFP binds to the antibodies. Antibodies to AFP, labelled with luminol prepared as described for the PTH assay are then added. After an overnight incubation period, the tubes are emptied and washed twice in phosphate (0.05M pH 7.4) buffered saline containing 0.1% bovine serum albumin. The tubes are transferred to the photon counter and the light emitting reaction is triggered as in the PTH assay. The amount of light emitted is a function of the amount of luminol present and hence of the concentration of AFP in the samples.

7. Homogeneous Assay of Cyclic AMP

An antibody to cyclic AMP (or GMP) is labelled with luminol as described in Examples 2 and 3. Succinyl cyclic AMP (or GMP) is labelled with fluorescein. The labelled antibody is reacted with the labelled cyclic AMP (or GMP) in reaction tube at pH 7.4. Peroxidase (10 mU) and hydrogen peroxide (1 mM) are added and the light emission at 540 nm measured. Emission at this wavelength can only derive from the fluorescein labelled component which is bound to antibody. Unbound antibody will emit at a different wavelength (i.e. 460 nm).

The light emitted by luminol is absorbed by fluorescein most efficiently when the two molecules are in close proximity i.e. <100 Å. Thus the wavelength shift occurs only when labelled cyclic AMP and antibody are bound together. The same reaction may be carried out when the cyclic AMP is labelled with luminol and the antibody with fluorescein.

We claim:

1. A method of detecting or quantifying a substance of biological interest in a body fluid or tissue, in which a labelled binding reagent comprising an antibody, or binding protein, binding specifically to the substance, is linked with a label comprising one or more components which can participate in a luminescent reaction, the labelled binding reagent being immunologically purified and such that it is stable and its properties are not significantly altered by the label, the substance is subsequently contacted with the labelled binding reagent, and a luminescent reaction is subsequently triggered, the emitted light being sensed or measured to provide information concerning the substance of interest.

2. A method according to claim 1, in which the reaction is triggered chemically, by means of a chemical reagent or catalyst.

3. A method according to claim 2, in which the luminescent reaction is triggered by an oxidising agent, a catalyst, or a change in pH.

4. A method according to claim 1, in which the reaction is triggered physically.

5. A method according to claim 1, in which the substance of interest, to which the labelling component is linked, is a protein, hapten, hormone, metabolite, nucleic acid, or steroid.

6. A method according to claim 1, constituting a protein binding assay, in which the binding protein or a standard substance is linked with said label.

7. A method according to claim 1, constituting a method of locating substances histologically.

8. A method according to claim 1, in which said label is a compound of the general formula:

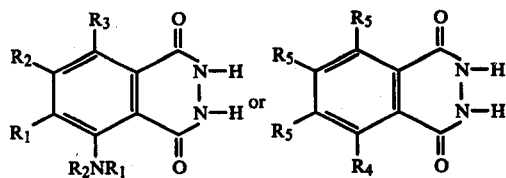

in which each of $R_1$, $R_2$ and $R_3$ is H, $C_1$-$C_{10}$ optionally substituted alkyl or alkenyl, amino, substituted amino, carboxyl or hydroxyl, each of $R_4$ and $R_5$ is the same as $R_1$, $R_2$ or $R_3$, or is a diazo-linkage, a hemi-dicarboxylate linkage, an amide linkage, an organic acid halide, or an isothiocyanate group, with the proviso that at least one of $R_1$ to $R_5$ is amino or substituted amino.

9. A method according to claim 1, in which said label is a compound of the general formula:

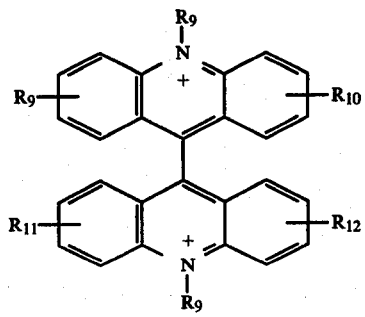

in which each of $R_9$, $R_{10}$ and $R_{11}$ is H, $C_1$-$C_{10}$ optionally substituted alkyl or alkenyl, amino, substituted amino, carboxyl or hydroxyl, each of $R_{11}$ and $R_{12}$ is the same as $R_9$, $R_{10}$ or $R_{11}$, or is a diazo-linkage, a hemi-dicarboxylate linkage, an amide linkage, an organic acid halide, or an isothiocyanate group, with the proviso that at least one of $R_9$ to $R_{12}$ is amino or substituted amino.

10. A method according to claim 1, in which said label is a compound of the general formula:

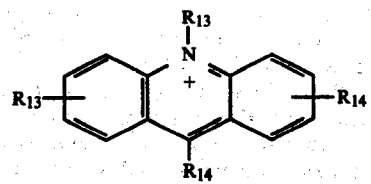

in which each of $R_{13}$ and $R_{14}$ is H, $C_1$-$C_{10}$ optionally substituted alkyl or alkenyl, amino, substituted amino, carboxyl or or hydroxyl, or is a diazo-linkage, a hemi-dicarboxylate linkage, an amide linkage, an organic acid halide, or an isothiocyanate group, with the proviso that either $R_{13}$ or $R_{14}$ is amino or substituted amino.

11. A method according to claim 1, in which said label is a compound of the general formula:

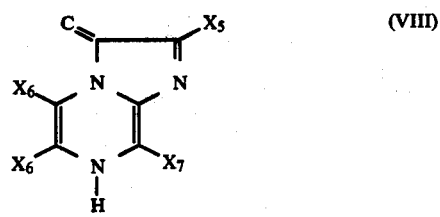

(VIII)

in which each of $X_5$, $X_6$ and $X_7$ is H, $C_1$-$C_{10}$ optionally substituted alkyl or alkenyl, amino, substituted amino, carboxyl or hydroxyl, or is a diazo-linkage, a hemi-dicarboxylate linkage, an amide linkage, an organic acid halide, or an isothiocyanate group, with the proviso that at least one of $X_5$ to $X_7$ is amino or substituted amino, or is

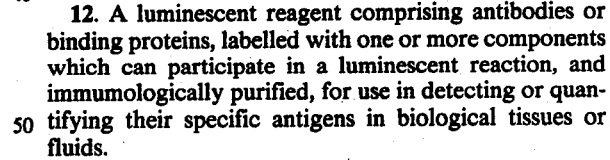

12. A luminescent reagent comprising antibodies or binding proteins, labelled with one or more components which can participate in a luminescent reaction, and immunologically purified, for use in detecting or quantifying their specific antigens in biological tissues or fluids.

13. A reagent according to claim 12, in which the antibodies are sheep- (anti-rabbit IgG), sheep- (anti-guinea pig IgG), guinea pig IgG, sheep IgG, goat IgG and donkey IgG.

14. A luminescent reagent according to claim 12, in which at least 60% of the antibodies are capable of binding to corresponding antigens.

15. A method of preparing a luminescent reagent according to claim 12, in which a medium containing said antibodies is contacted with corresponding antigens to cause antibody-antigen association, said luminescent label being added before or after association occurs, and said labelled antibodies are subsequently dissociated from said antigens.

16. A method according to claim 15, in which said antigens are initially linked to a solid-phase immunoadsorbent.

17. A method according to claim 16, in which said solid-phase immuno-adsorbent is used to purify said antibodies which have been previously labelled in solution by contacting with said label.

18. A method of carrying out an assay, in which a medium containing the substance of interest, is contacted with antibodies so that the antibodies selectively bind the substance, the product of the reaction is subsequently contacted with labelled antibodies according to claim 12, and after removal of unreacted labelled antibodies a luminescent reaction is triggered, the amount of substance of interest which is present being indicated by the amount of luminescence.

19. A method according to claim 18, in which said substance of interest is bound to said antibodies on a solid phase.

20. A method according to claim 19, in which said solid phase is cellulose powder or the wall of a reaction vessel.

* * * * *